US006737535B2

(12) United States Patent
Kumar, T.K.

(10) Patent No.: US 6,737,535 B2
(45) Date of Patent: May 18, 2004

(54) TRANS-LUTEIN ENRICHED XANTHOPHYLL ESTER CONCENTRATE AND A PROCESS FOR ITS PREPARATION

(75) Inventor: Sunil Kumar, T.K., Angamally (IN)

(73) Assignee: Kancor Flavours and Extracts Limited, Kerala (IN)

( * ) Notice: Subject to any disclaimer, the term of this patent is extended or adjusted under 35 U.S.C. 154(b) by 0 days.

(21) Appl. No.: 10/209,185

(22) Filed: Jul. 30, 2002

(65) Prior Publication Data

US 2003/0229142 A1 Dec. 11, 2003

(30) Foreign Application Priority Data

Jun. 5, 2002 (IN) .................................. 420/MAS/2002

(51) Int. Cl.$^7$ ................................. C07C 1/00
(52) U.S. Cl. .......................................... 554/21; 554/20
(58) Field of Search ...................................... 554/21, 20

(56) References Cited

U.S. PATENT DOCUMENTS

| | | | |
|---|---|---|---|
| 3,539,686 A | 11/1970 | Rosenberg | |
| 4,048,203 A | 9/1977 | Philip | |
| 5,382,714 A | 1/1995 | Khachik | |
| 5,648,564 A | 7/1997 | Ausich et al. | |
| 6,191,293 B1 | 2/2001 | Levy | |
| 6,221,417 B1 | 4/2001 | Sas et al. | |
| 6,262,284 B1 | 7/2001 | Khachik | |
| 6,313,169 B1 | 11/2001 | Bowen et al. | |
| 6,329,557 B1 | 12/2001 | Rodriguez et al. | |
| 6,380,442 B1 | 4/2002 | Madhavi et al. | |
| 2003/0130531 A1 * | 7/2003 | Sadano et al. | 554/9 |

FOREIGN PATENT DOCUMENTS

| | | |
|---|---|---|
| DE | 1 224 597 | 7/1962 |
| WO | 99/20587 | 4/1999 |
| WO | 99/54408 | 10/1999 |

OTHER PUBLICATIONS

Riddick, et al., "Organic Solvents", Techniques of Chemistry, vol. II, 4th Edition, 1986.
Tyczkowski, et al., "Research Note: Prepartion of Purified Lutein and its Diesters from Extracts of Marigold (*Tagetes erecta*)", Poultry Science, vol. 70, pp. 651–654, 1991.
Subagio, et al., "Stability of Lutein and its Myristrate Esters", Biosci. Biotechnol. Biochem, vol. 63, No. 10, pp. 1784–1786, 1999.
Hadden, et al., "Carotenoid Composition of Marigold (*Tagetes erecta*) Flower Extract Used as Nutritional Supplement", J. Agricultural Food Chemistry, vol. 47, pp. 41189–4194, 1999.
Herbst, et al., "Evalution of the Bioavailability of Lutein (L) and Lutein Diesters (LD) in Humans", FASEB Journal abstracts no 11, 2587, 1997.

Breithaupt, et al., "Carotenoid Esters in Vegetables and Fruits: A Screening with Emphasis on β–Cryptoxanthin Esters", J. Agric. Food Chem, vol. 49, pp. 2064–2070, 2001.
Khachik, et al., "Separation and Identification of Carotenoids and Carotenol Fatty Acid Esters in Some Squash Products by Liquid Chromatography. 2. Isolation and Characterization of Carotenoids and Related Esters", J. Agric. Food Chem., vol. 36, pp. 938–946, 1988.
Seddon, et al., "Dietary Carotenoids, Vitamins A,C, and E, and Advanced Age–Related Macular Degeneration", JAMA, vol. 272, No. 18, 1413–1420, Nov. 1994.
Stahl, et al., "Antioxidant Food Supplements in Human Health", Academic Press, 184–201, 1999.
Khachik, et al., "Lutein, Lycopene, and Their Oxidative Metabolites in Chemoprevention of Cancer", Journal of Cellular Biochemistry, Supplement 22, 236–246, 1995.
Antony, et al., "Lutein A natural colourant and a phytonutrient for eye health protection", The World of Food Ingredients, 64–67, Apr./May 2001.
Gau et al., "Mass Spectrometric Identification of Xanthophyll Fatty Acid Esters from Marigold Flowers (Tagetes Erecta)Obtained by High–proformance Liquid Chromatography and Craig Counter–Current Distribution", Journal of Chromatography, vol. 262, 277–284, 1983.
Khachik, et al., "Solution and Structural Elucidation of (13Z, 13'Z, 3R, 3'R, 6'R)—Lutien from Marigold Flowers, Kale, and Human Plasma", J. Agric. Food Chem., vol. 47, 455–461, 1999.
Moeller, et al., "The Potential Role of Dietary Xanthophylls in Cataract and Age–Relayed Macular Degeneration", Journal of the American College of Nutrition, vol. 19, No. 5, 522S–527S, 2000.
Bone, et al., "Distribution of Lutein and Zeaxanthin Steroisomers in the Human Retina", Exp. Eye Res., vol. 64, 211–218, 1997.
Cooper, et al., "Dietary Carotenoids and Certain Cancers, Heart Disease and Age Realted Macular Degeneration:A Review of Recent", Nutr. Rev., vol. 57, 201–214, 1999.

(List continued on next page.)

*Primary Examiner*—Deborah D. Carr
(74) *Attorney, Agent, or Firm*—Merchant & Gould P.C.

(57) ABSTRACT

A novel xanthophyll esters concentrate including a composition containing lutein and zeaxanthin fatty acid esters wherein the composition contains by weight 90–95% of trans-lutein esters, 0–5% of cis-lutein esters and 3.5 to 6% of zeaxanthin esters. More particularly, a process is provided for the preparation of the above concentrate employing ketonic solvents. The novel trans-lutein enriched xanthophyll ester concentrate is useful for human consumption, either as nutraceuticals, as nutritional supplements, as food additives and also for coloring animal feeds. The concentrate has better stability and bioavailability.

14 Claims, No Drawings

OTHER PUBLICATIONS

Slattery, et al., "Carotenoids and colon cancer", Am. J. Clin. Nutr., vol. 71, 575–582, 2000.

Howard et al., "Do Hydroxy–Carotenoids Prevent Coronary Heart Disease?: A Comparison Between Belfast and Toulouse", Int. J. Vita. Nutr. Res., vol. 66, 113–118, 1996.

Craft, et al., Relative Solubility, Stability, and Absorptivity of Lutein and β–Carotene in Organic Solvents, J. Agric. Food Chem, vol. 40, 431–434, 1992.

AOAC—16th edition, method 970.64, Vitamins and Other Nutrients, Chapter 45, 5–6, 1996.

Database WPI, Section Ch, Week 200235, Dewent Publications Ltd., London, GB, Class D23, AN 2002–311245, XP002252730.

* cited by examiner

TRANS-LUTEIN ENRICHED XANTHOPHYLL ESTER CONCENTRATE AND A PROCESS FOR ITS PREPARATION

INTRODUCTION

The present invention relates to a novel trans-lutein enriched xanthophyll ester concentrate and a process for its preparation. The present invention, more particularly, provides a novel trans-lutein enriched xanthophyll ester concentrate, in which the xanthophyll esters comprise 90–95% of trans-lutein esters, 0–5% of cis-lutein esters and 3.5–6% of zeaxanthin esters. The novel trans-lutein enriched xanthophyll esters concentrate of the present invention is useful for human consumption, either as nutraceuticals, as nutritional supplements, as food additives and also for colouring feeds. As nutraceuticals, the concentrate of the present invention has particular use as an agent for protecting against eye diseases due to aging, cataract and macular degeneration and for reducing the risk of developing certain diseases like cancer, cardiovascular diseases, etc., as well as for use as an antioxidant. The concentrate of the present invention also has better stability and bio-availability.

The invention also provides a process for the preparation of the above novel translutein enriched xanthophyll ester concentrate from oleoresin, especially from marigold oleoresin.

BACKGROUND OF THE INVENTION

Carotenoids are one of the most abundant kind of pigments widely distributed among plants and are considered to be non-toxic to human consumption. Xanthophyll esters are included as a group of these carotenoids. They essentially are di- or mono-fatty acid esters of the carotenoids consisting chiefly of di-palmitate, di-myristate, di-stearate as lutein and zeaxanthin. Zeaxanthin ester is a pigment contained in berries such as those of genus Lycium chinense (Chinese wolfberries) and Physalis. Lutein esters are pigments that give the yellow/red color to fruits, such as oranges, peaches, papayas, mangoes, etc. Lutein esters also are present in many floral parts particularly marigold flowers of genus Tagetes. Xanthophyll esters are generally found in nature as tran-sxanthophyll isomers and also in cis-isomeric form in trace amounts mainly formed due to adverse conditions of heat and light. Lutein esters of higher purity and naturally preserved trans-isomeric form are preferred for use in human requirements because of their better stability and bioavailability.

The above carotenoids mainly being fat-soluble have limited applications in foods. Dihydroxy carotenoids (xanthophylls), lutein and zeaxanthin are compounds valued as poultry feed colourant and as a health nutritional supplement. Xanthophyll esters form the major colouring component in marigold flowers and its extracts.

Marigold flowers are one of the richest sources of trans-lutein esters found in nature. Dried and ground marigold flowers have been used commercially for more than three decades as a pigmenting agent in poultry and animal feeds and as a food coloring agent. For many years, it has been used as the starting material for the production of marigold extracts containing xanthophyll esters, which is a commercially important ingredient. Reference in this context may be made to U.S. Pat. No 3,539,686, (1970) and German Patent No 1,224,597.

Recently, these and other carotenoid esters both in mono- and di-ester forms have been reported to be naturally occurring in several fruits and vegetables (D. E. Breithaupt and A. Bamedi; *Journal of Agricultural Food Chemistry*, Vol. 49, 2064–2070, (2001); F. Khachik, G. R. Beecher and W. R. Lusby, *Journal of Agricultural Food Chemistry*, Vol. 36,938–946, 1988). Xanthophyll esters with higher amounts of trans-lutein content have gained importance, and are preferred because of their natural occurrence in foods, better stability and bio-availability (Bowen and Clark, U.S. Pat. No. 6,313,169, November 2001; Herbst et al. *FASEB Journal Abstract No.* 11, 2587, (1997); A. Subagio, H. Wakaki and N. Morita, *Biosci.Biotechnol.Biochem.*, 63 (10), 1784–1786, (1999)). Further, the colouring power of trans-lutein (absorption maximum at 474 nm) is superior to cis-lutein (absorption maximum at 468 nm)(W. L. Hadden, R. H. Watkins, L. W. Levy, E. Regalado, D. M. Rivadeneira, R. B. van Breemen and S. J. Schwartz, *Journal of Agricultural Food Chemistry*, Vol. 47,4182–4194 (1999)).

U.S. Pat. No. 4,048,203, (1977) (Philip) describes a process for the extraction of lutein esters starting from marigold extract prepared by treating dried and ground marigold petals (1 kg) with petroleum ether at room temperature. The extract was obtained by removal of the solvent under vacuum at 50° C. The oleoresin (65 g) obtained through this process was dissolved in hot isopropanol at 75° C. and the solution was filtered through a sintered glass funnel to remove undissolved materials. The filtrate was then cooled to 15° C. and the precipitated lutein fatty acid esters were recovered by filtration through a sintered glass funnel. The esters were dried under a vacuum at 30° C. to yield 21 g lutein fatty acid esters with a 51% lutein esters content.

However, in this patent there is no indication of the content of trans and/or cis-isomeric forms. Further, due to alkanol precipitation at a high temperature, a considerable amount of trans-lutein esters is converted into cis-isomeric form, which is considered undesirable for use as human nutritional supplements. Further, the tinctorial shade/hue of the cis-isomeric form is relatively poor.

Tycozkowski and Hamilton (*Poultry Science*, 70, 651–654 (1991)) reported a process for the preparation of trans-lutein di-esters by reacting free lutein (prepared from marigold oleoresin after saponification) with an acyl chloride. In this process, a saponified extract of marigold petals containing 14.70 mg lutein per gram was the starting material. 1 g of the material was added with 10 ml of a solvent mixture HAET (hexane: acetone: toluene: absolute alcohol in the ratio 10:7:7:6 respectively). The mixture was stirred well followed by the addition of 10 ml of hexane and then 7 ml of 10% aqueous sodium sulfate. After allowing the mixture to stand for 1 hour, the clear top layer was separated, condensed under nitrogen atmosphere to one-third its initial volume, and placed at a temperature of 4° C. until crystals were formed. The crystals were filtered, washed with cold hexane, and dissolved in a minimal amount of warm hexane: acetone (80:20 v/v) for recrystallization. The final crystals were stored under nitrogen gas in the dark.

Lutein di-esters were prepared by reaction of free lutein with acyl chloride. In one example, 20 mg of lutein was dissolved in 15 ml pyridine followed by the addition of 1 ml of palmitoyl chloride (99+%), and the mixture was incubated at 50° C. for 2 hours. Later the reaction mixture was transferred to a separatory funnel with the addition of 30 ml of HAET solution and hexane. The mixture was then washed twice with equal volumes of 10% aqueous sodium sulfate ($Na_2SO_4$) and twice with distilled water. After drying the upper layer with anhydrous sodium sulfate ($Na_2SO_4$), the solvent was evaporated under nitrogen gas and lutein di-ester residue was stored under nitrogen gas in the dark at −20° C.

However, this synthesis-based method is not preferred because of the presence of associated impurities and non-availability of the naturally occurring lutein di-esters (xanthophyll esters). Therefore, the product resulting from the method is not equivalent to the similar product produced or derived from a natural source, such as marigold flowers or their extracts.

Recently, U.S. Pat. No. 6,191,293; (2001) to Levy described a method for the preparation of trans-xanthophyll ester concentrates having a trans-xanthophyll esters content at least 4 times and preferably at least nine times greater than the cis-xanthophyll esters content. The patent reports that xanthophyll esters concentrates having a total xanthophyll esters content of at least 40% by weight and preferably greater than about 55% by weight are obtained by the process disclosed therein.

The method of preparation comprises contacting plant material containing xanthophyll esters with a hydrocarbon solvent for a time sufficient to extract xanthophyll esters from the plant material, separating the hydrocarbon solvent and extract dissolved therein from the remaining plant material, evaporating the hydrocarbon solvent from the dissolved extract to obtain a crude xanthophyll ester concentrate, admixing the crude xanthophyll esters concentrate with an alcohol, preferably isopropanol, at approximately ambient temperature to dissolve non xanthophyll impurities and cis xanthophyll esters from the crude trans-xanthophylls concentrate to obtain the purified trans-xanthophyll esters concentrate. In a preferred embodiment of the above U.S. Patent, the plant materials used are marigold flowers, preferably the corollas of the flowers.

The method disclosed in the above patent describes an example wherein one kilogram of dried marigold corollas (lutein esters content 2.90% by weight) yielded 100 g of oleoresin by extraction with 8 liters of hexane. The oleoresin showed 27.9% lutein esters by weight and 75:25 trans-:cis-lutein isomer ratio (by HPLC peak heights). The oleoresin was stirred for three hours with 200 g isopropanol at 20° C. and after filtration and removal of the solvent yielded 20 g of lutein esters concentrate with 69% lutein esters content (by a spectrophotometric method) and trans-:cis-lutein isomer ratio 90:10 (by HPLC method).

In the above method, admixing the oleoresin with isopropanol at room temperature helps preferential dissolution of cis-isomers in isopropanol and thereby the lutein esters concentrate gets enriched with trans-lutein esters content with a trans-:cis-ratio 90:10. The method employs removal of isopropanol residue by applying a vacuum at room temperature. Since isopropanol has a boiling point around 82.5° C., its removal to meet the health requirements involves long periods of time, making the process time consuming and laborious.

It is now well recognized that trans-xanthophyll esters containing higher amounts of trans-lutein content possess better stability and bio-availability. Further, it also has higher coloring power (absorption maximum of trans-lutein esters at 474 nm and cis-lutein esters at 468 nm). Hence, there currently is a greater demand for xanthophyll esters concentrate having higher amounts of trans-isomer and consequently the commercial importance of such a product has gained importance globally. Therefore, we directed our research efforts towards development of a xanthophyll ester concentrate having higher amounts of trans-isomer and negligible or trace amount of cis-isomer, and a process for the preparation of such a concentrate.

SUMMARY

Therefore, the main objective of the present invention is to provide a novel xanthophyll ester concentrate having higher amounts of trans-isomer and negligible or trace amount of cis-isomer which is useful for human consumption, as a nutraceutical, as nutritional supplements, as food additives, for colouring foods and feeds, and which has better stability and bio-availability.

Another objective of the present invention is to provide a novel trans-xanthophyll ester concentrate predominantly comprising a composition containing lutein and zeaxanthin fatty acid esters wherein the composition contains by weight 90–95% of trans-lutein esters, 0–5% of cis-lutein esters and 3.5–6% of zeaxanthin esters, which is useful for human consumption, as nutraceuticals, as nutritional supplements, as food additives and also for colouring foods & feeds and which has better stability and bio-availability.

Yet another objective of the present invention is to provide a process for the preparation of a novel trans-xanthophyll ester concentrate predominantly comprising a composition containing lutein and zeaxanthin fatty acid esters wherein the composition contains by weight 90–95% of trans-lutein esters, 0–5% of cis-lutein esters and 3.5–6% of zeaxanthin esters, and which has better stability and bio-availability.

Still another objective of the present invention is to provide a process for the preparation of a novel trans-xanthophyll ester concentrate predominantly comprising a composition containing lutein and zeaxanthin fatty acid esters wherein the composition contains by weight 90–95% of trans-lutein esters, 0–5% of cis-lutein esters and 3.5–6% of zeaxanthin esters, and which has better stability and bio-availability from oleoresin such as marigold oleoresin.

The invention has been developed based on our finding that by preserving the natural trans-isomeric form in xanthophyll esters extract comprising a composition containing lutein and zeaxanthin fatty acid esters and by the selective removal of the cis-lutein esters and other undesirable impurities therefrom, a novel xanthophyll ester concentrate predominantly containing trans-lutein esters with negligible levels of the cis-lutein esters and devoid of the undesirable impurities can be obtained.

We have found that by following the above method, a novel trans-xanthophyll ester concentrate can be obtained, which contains lutein and zeaxanthin fatty acid esters comprising by weight 90–95% trans-lutein esters. Such a concentrate would have higher pigmenting properties and greater bio-availability of trans-lutein esters. Consequently, the new concentrate would be very useful as nutraceuticals, such as those explained earlier, as human nutritional supplements and as a coloring agent for food and animal feeds.

With the above objective in mind we studied in depth the effectiveness of dissolving specific solutes in specific solvents. Generally, the effectiveness of dissolving specific solutes in specific solvents is governed by parameters including polarity of the solute, solubility parameter of the solvent, temperature, pressure, solute to solvent ratio, mixing time, etc. We observed that when aliphatic ketonic solvents, such as 2-propanone, 2-butanone and 2-pentanone, or their mixtures, are mixed with extracts containing xanthophyll esters, comprising a composition containing lutein and zeaxanthin fatty acid esters, there is a preferential dissolution of cis-isomeric lutein esters and the impurities such as triglycerides, waxes, etc., in the solvent, resulting in a concentrate enriched with trans-lutein esters.

It can be seen from the literature (J A Riddick et al., *Organic Solvents Tech Organic Chemistry*, Vol. II, 5$^{th}$ Edition, John Wiley and Sons, 1986) that the aliphatic ketones, such as 2-propanone, 2-butanone, 2-pentanone and their mixtures, have a solubility parameter values around 10 which is in between the solubility parameter values of nonpolar solvents, such as hexane (around 7) and polar solvents, such as methanol (around 14.5). One reason for the unique preferential and selective solubility of the cis-isomer and the impurities in the above ketonic solvents may be due to the above characteristics of the solvents, and also the unsymmetrical nature of the cis-isomer and/or due to the synergistic effects of the above phenomena. The selection of the above mentioned ketonic solvents, among the wide range of ketonic solvents is based on critical factors such as safety and health regulations, ease of handling, low boiling point commercial considerations and more importantly the above functional property of selectivity. It is also to be mentioned here that the use of such ketonic solvents have not hitherto been used for the selective dissolution of the cis-isomers.

Accordingly, the present invention provides a novel xanthophyll ester concentrate, which is useful for human consumption, either as nutraceuticals or as food additives and also for coloring foods and animal feeds and which has better stability and bioavailability predominantly comprising a composition containing lutein and zeaxanthin fatty acid esters wherein the composition contains by weight 90–95% of trans-lutein esters, 0–5% of cis-lutein esters and 3.5–6% of zeaxanthin esters.

According to another embodiment of the present invention there also is provided a process for the preparation of the above defined xanthophyll ester concentrate which comprises:

(a) admixing an extract or oleoresin containing xanthophyll esters containing lutein and zeaxanthin fatty acid esters with an aliphatic ketonic solvent selected from the group of 2-propanone, 2-butanone, 2-pentanone, or mixtures thereof at a temperature in the range of 10° C. and 30° C. and agitating the mixture by stirring to selectively solubilize the non-xanthophyll ester impurities and the cis-lutein esters and lipids present therein and simultaneously enriching the trans-lutein esters content of the resulting mixture;

(b) filtering the resulting mixture to obtain a trans-lutein enriched xanthophyll esters concentrate in a solid form;

(c) drying the concentrate under a vacuum at room temperature; and (e) preserving the concentrate at a temperature below 20° C. in an inert atmosphere and in airtight opaque containers to prevent degradation of the concentrate.

In a preferred embodiment of the invention the weight-to-volume ratio of extract or oleoresin containing xanthophyll esters from the plant source to the ketonic solvent used ranges from 1:3 to 1:15. The preferred extract or oleoresin containing xanthophyll esters containing lutein and zeaxanthin fatty acid esters used is marigold oleoresin.

The temperature employed for admixing the extract with the ketonic solvent may preferably be in the range of 15° C. to 30° C.

The period of agitation in step (a) may be for a period ranging from 2 to 12 hours, and more preferably around 10 hours.

Preferably, the resultant concentrate is preserved suitably at low temperature namely below 20° C. in an inert atmosphere and in airtight opaque containers to prevent degradation of the concentrate.

The trans-lutein enriched xanthophyll esters concentrate of the present invention can be converted, if desired, into products, such as beadlets, capsules, pellets, ointments, soft gelatin capsules, tablets, chewable tablets, and lotions/liquid preparations, etc. by conventional methods.

DETAILED DESCRIPTION OF THE INVENTION

The commercially produced food grade marigold oleoresin using hexane as an extractant can be used as the starting material for the process of the present invention. As explained earlier the marigold flower (Tagetes erecta) is known to be a rich source for obtaining xanthophyll esters and its derivatives and particularly for trans-lutein esters. In recent years, the cultivation of marigold flowers has largely increased producing quality marigold flowers in many parts of South India. There are many commercial manufacturers producing marigold oleoresin containing around 20–25% xanthophyll esters.

In one preferred embodiment of the present invention, commercially procured/ processed marigold oleoresin containing trans-lutein and cis-lutein content as 66% and 25%, respectively is admixed with a ketonic solvent, such as 2-propanone, 2-butanone or their mixtures, preferably 2-propanone under stirring at controlled temperature in the range between 15° C. and 30° C., preferably 25° C., so as to remove the impurities and as well as to precipitate the trans-lutein esters enriched xanthophyll esters, followed by filtration and washing with the same solvent. The material resulting from filtration and washing is dried at ambient temperature, under a vacuum to obtain a concentrate containing by weight 90–95% of trans-lutein esters, 0–5% of cis-lutein esters and 3.5–6% of zeaxanthin esters.

We also have observed that the resulting enriched trans-lutein concentrate has improved visual appearance which is confirmed by higher $L^*$, $a^*$, $b^*$ values measured on a Hunter Colorimeter.

By the process according to the present invention, a xanthophyll ester concentrate can be prepared having a trans-:cis-lutein isomer ratio of at least 18:1, and preferably having a ratio of at least 18:1 to 475:1, and xanthophyll ester content 60–80% by weight in the concentrate as compared to the reported corresponding values ranging from 4:1 to 9:1 and 41 to 69% by weight, respectively (Levy U.S. Pat. No. 6,191,293, (2001)). Further, a trans-xanthophyll ester concentrate can be prepared with a trace amount of cis-isomer or with the removal of cis-isomer such that cis-isomer is not present in the resulting concentrate.

Preferably, the novel xanthophyll ester concentrate of the present invention is preserved at a temperature below 20° C. in an inert atmosphere and in airtight opaque containers to prevent the degradation of the concentrate.

The details of the invention are given in the examples below which are provided solely to illustrate the invention only and therefore should not be construed to limit the scope of the present invention.

In this context, it is to be noted that there are no established or recommended procedures for direct analysis of total xanthophyll ester content and its isomeric composition such as trans- and cis- in a given sample. This difficulty is due to the fact that the ester concentrate is a mixture of several fatty acids esters of lutein and zeaxanthin, which are not easily separated in HPLC. Further, pure or reference standards of these esters are not available from reputed chemical suppliers.

Therefore the most widely adopted methodology consists of initial hydrolysis of the ester concentrate and measuring the colour of an aliquot of the solution at 474 nm using a spectrophotometer and expressing the same as xanthophyll content. From this value, xanthophyll ester content is calculated by multiplying by a factor of 2.

Later an aliquot of the above sample solution is analyzed by normal phase HPLC to obtain percentage areas of trans- & cis-isomers of lutein and zeaxanthin. The percentage area of each of the isomers corresponds to percentage by weight composition of its ester form in the concentrate.

In the following examples, we have used the above method for measuring xanthophyll ester content, cis- & trans-lutein esters content. We have also taken into account the relative percentage area between the trans & cis-isomers by HPLC method described above for calculating the trans- to cis-lutein ratio while defining the novel concentrate of the present invention.

EXAMPLE 1

A weighed quantity of marigold oleoresin (180 g) with a xanthophyll ester content of 21.80% by weight and showing trans-lutein, cis-lutein and zeaxanthin area percentages, by HPLC, of 64.24, 23.46 and 4.16, respectively, was transferred into an Erlenmeyer flask (1000 ml) followed by the addition of 720 ml of 2-propanone. This was stirred using a thermostatically controlled stirrer at 15° C. to 25° C. for a period of 5–10 hours. After an interval of every 2 hours, a sample was drawn, filtered and the dried precipitated material was analyzed for the ester content and the trans-:cis-ratio by HPLC. Finally, when the desired degree of purity had been achieved the solution containing the precipitate was filtered through a Buchner funnel and the precipitate was dried in a vacuum drier at ambient temperature.

The yield of the resulting concentrate was 18.19 g (yield 10.10%) and the analysis showed a xanthophyll ester content of 64.02% by weight, which was assayed by a spectrophotometric method, measuring at 474 nm. This xanthophyll ester concentrate showed area percentages, by HPLC, of 90.38 trans-lutein, 3.85 cis-lutein and 4.43, zeaxanthin, respectively. Visual examination showed this concentrate with an improved orange red color as compared to the starting material, which was dark brown in color.

EXAMPLE 2

157 g of commercial grade marigold oleoresin containing 21.38% xanthophyll ester content by weight, and containing trans-lutein, cis-lutein and zeaxanthin area percentages, by HPLC, of 65.59, 24.61 and 5.08, respectively, was transferred into an Erlenmeyer flask (1000 ml), and stirred with 540 ml of 2-propanone for a period of 10 hours at 15° C. to 25° C. After an interval of every 2 hours, a sample was drawn, filtered and the dried precipitated material was analyzed for the ester content and the trans-:cis-ratio by HPLC. Finally, when the desired degree of purity had been achieved the solution containing the precipitate was filtered through a Buchner funnel and the precipitate was dried in a vacuum drier at ambient temperature.

The yield of the resultant concentrate was found to be 17.2 g (yield 10.95%) with a xanthophyll esters content of 62.60% by weight, which was assayed by a spectrophotometric method, measuring at 474 nm. This xanthophyll ester concentrate showed area percentages, by HPLC analysis, of 92.20 trans-lutein, 2.33 cis-lutein and 4.40 zeaxanthin, respectively. Visual examination showed this concentrate with an improved orange red color as compared to the starting material, which was dark brown in color.

EXAMPLE 3

The experiment was performed using 180 grams of commercial grade marigold oleoresin containing 22.12% by weight xanthophyll esters content with trans-lutein, cis-lutein and zeaxanthin area percentages, by HPLC, of 67.05, 22.98 and 4.50, respectively, transferred into an Erlenmeyer flask (100 ml). 720 ml of 2-propanone was added and the mixture was stirred for a period of 10 hours at 15° C. The precipitated cake was filtered and again subjected to further purification by the addition of 350 ml of 2-propanone and stirring continued for a period of 2–3 hours and maintained at a temperature around 25° C. Finally, the concentrate obtained after filtration and drying was found to be 17.40 g (yield 9.67%). The xanthophyll ester content was 70.58%, which was assayed by a spectrophotometric method, measuring at 474 nm. This xanthophyll ester concentrate showed area percentages of trans-lutein 92.47, cis-lutein 2.32 and zeaxanthin 4.31, respectively, by HPLC analysis. Visual examination showed this concentrate showed with an improved orange red color as compared to the starting material, which was dark brown in color.

EXAMPLE 4

100 g of marigold oleoresin obtained from commercial scale production batch having a xanthophyll esters content of 23.10% by weight and containing area percentages, by HPLC, of trans-lutein 67.23, cis-lutein 22.08 and zeaxanthin 5.18 was taken. This was admixed with 2-propanone, and was subjected to controlled stirring in an Erlenmeyer flask at a temperature between 15° C. to 28° C. to remove impurities as well as to precipitate the trans-lutein rich xanthophyll esters. The mixture was filtered and washed. The concentrate was dried under a vacuum at room temperature.

The yield of the concentrate was 14.10 grams (yield 14.10%) with the xanthophyll esters content being 61.18% by weight, which was assayed by a spectrophotometric method, measuring at 474 nm. This xanthophyll ester concentrate showed area percentages, by HPLC, of trans-lutein 93.50, cis-lutein 1.56 and zeaxanthin 4.17, respectively.

The resultant product was subjected to further purification by treating with 150 ml (twice) of the same ketonic solvent, namely 2-propanone, and stirring for a period of 5–10 hours, at a temperature of 15° C. to 25° C. The resultant mixture was filtered and dried under a vacuum. The yield was 9.65 grams (9.65%), and the xanthophyll esters content was 66.32% by weight, which was assayed by a spectrophotometric method, measuring at 474 nm. This xanthophyll ester concentrate showed area percentages, by HPLC, of trans-lutein 94.57, no cis-lutein (0%) and zeaxanthin 4.45, respectively. Visual examination showed this concentrate with an improved orange red color as compared to the starting material, which was dark brown in color.

EXAMPLE 5

A weighed quantity of marigold oleoresin (102 g) with an xanthophyll ester content of 23.06% and trans-lutein, cis-lutein and zeaxanthin area percentages, by HPLC, of 68.14, 20.77 and 5.18, respectively. This oleoresin was transferred into an Erlenmeyer flask (1000 ml) followed by the addition of 720 ml of 2-propanone. This was stirred using a thermostatically controlled stirrer at 15° C. to 25° C. for a period of 5–10 hours. After an interval of every 2 hours a sample was drawn, filtered and the dried precipitated material was analyzed for the ester content and the trans-:cis-ratio by HPLC. Finally, when the desired degree of purity had been achieved the solution containing the precipitate was filtered through a Buchner funnel and the precipitate was dried in a vacuum drier at ambient temperature.

The yield of the resulting concentrate was 14.77 g (14.48%) and the analysis showed a xanthophyll ester content of 61.60%, which was assayed by a spectrophotometer, measuring at 474 nm. This xanthophyll ester concentrate contained area percentages, by HPLC, of trans-lutein 92.03, cis-lutein 1.95 and zeaxanthin 5.34, respectively. Visual examination showed this concentrate with an improved orange red color as compared to the starting material, which was dark brown in color.

EXAMPLE 6

A weighed quantity of marigold oleoresin (150.3 g) with a xanthophyll ester content of 23.10% and trans-lutein, cis-lutein and zeaxanthin area percentages, by HPLC, of 67.23, 22.08 and 5.18, respectively, was transferred into an Erlenmeyer flask (1000 ml) followed by the addition of 750 ml of 2-propanone. This was stirred using a thermostatically controlled stirrer at 15° C. to 25° C. for a period of 5–10 hours. After an interval of every 2 hours, a sample was drawn, filtered and the dried precipitated material was analyzed for the ester content and the trans-:cis-ratio by HPLC. Finally, when the desired degree of purity had been achieved the solution containing the precipitate was filtered through a Buchner funnel and the precipitate was dried in a vacuum drier at ambient temperature.

The yield of the resulting concentrate was 20.10 g (13.37%) and the analysis showed a xanthophyll ester content of 59.26%, which was assayed by a spectrophotometric method, measuring at 474 nm. This xanthophyll ester concentrate contained area percentages, by HPLC, of trans-lutein 92.71, cis-lutein 1.40 and zeaxanthin 5.11, respectively. Visual examination showed this concentrate with an improved orange red color as compared to the starting material, which was dark brown in color.

EXAMPLE 7

A weighed quantity of marigold oleoresin (30.80 g) with a xanthophyll ester content of 23.10% and trans-lutein, cis-lutein and zeaxanthin area percentages, by HPLC, of 67.23, 22.08 and 5.18, respectively, was transferred into an Erlenmeyer flask (500 ml) followed by the addition of 125 ml of 2-butanone. This mixture was stirred using a thermostatically controlled stirrer at 15° C. to 25° C. for a period of 10 hours. After an interval of every 2 hours, a sample was drawn, filtered and the dried precipitated material was analyzed for the ester content by a spectrophotometric method and the trans-:cis-ratio by HPLC. Finally, when the desired degree of purity had been achieved the solution containing the precipitate was filtered through a Buchner funnel and the precipitate was dried in a vacuum drier at ambient temperature.

The yield of the resulting concentrate was 3.12 g (yield 10.13%) and the analysis showed a xanthophyll ester content of 46.98% by weight, which was assayed by a spectrophotometric method, measuring at 474 nm. This xanthophyll ester concentrate showed area percentages, by HPLC, of trans-lutein 92.33, cis-lutein 3.09 and zeaxanthin 3.72, respectively. Visual examination showed this concentrate with an improved orange red color as compared to the starting material, which was dark brown in color.

EXAMPLE 8

A weighed quantity of marigold oleoresin (30.28 g) with a xanthophyll ester content of 23.10% by weight and trans-lutein, cis-lutein and zeaxanthin area percentages, by HPLC, of 67.23, 22.08 and 5.18, respectively, was transferred into an Erlenmeyer flask (500 ml) followed by the addition of 125 ml of a mixture containing equal volumes of 2-propanone and 2-butanone. This was stirred using a thermostatically controlled stirrer at 15° C. to 25° C. for a period of 5–10 hours. After an interval of every 2 hours, a sample was drawn, filtered and the dried precipitated material was analyzed for the ester content and the trans: cis ratio by HPLC. Finally, when the desired degree of purity had been achieved the solution containing the precipitate was filtered through a Buchner funnel and the precipitate was dried in a vacuum drier at ambient temperature.

The yield of the resulting concentrate was 4.34 g (yield 14.35%) and the analysis showed a xanthophyll ester content of 46.82% by weight, which was assayed by a spectrophotometric method, measuring at 474 nm. This xanthophyll ester concentrate contained area percentages, by HPLC, of trans-lutein 92.68, cis-lutein 2.81 and zeaxanthin 3.83, respectively. Visual examination showed this concentrate with an improved orange red color as compared to the starting material, which was dark brown in color.

The concentrate of the present invention has by weight 90 to 95% of trans-lutein esters in its natural form having enhanced stability and bioavailability. The ratio of trans-lutein isomer to cis-lutein isomer ranging from at least 18:1 to 475:1, or the cis-lutein isomer-free product as obtained in the concentrate of the present invention, from the process claimed in the present invention is a clearly demonstrable and substantial improvement over the inventions presented in prior art or prevalent in commerce.

The concentrate of the present invention is suitable for human consumption either as a nutraceutical or as a food additive and also for colouring food and feed materials.

The concentrate of the present invention can be converted, if desired, into products, such as beadlets, capsules, pellets, ointments, soft gelatin capsules, tablets, chewable tablets, lotions/liquid preparations, etc., by conventional methods.

It is our intention to cover all the possible legitimate modifications falling within the broad spectrum of the invention as disclosed herein and therefore the invention also covers such modifications.

What is claimed is:

1. A novel xanthophyll ester concentrate, which is useful for human consumption, either as a nutraceutical or as food additives and also for coloring food and animal feeds, and which has better stability and bio-availability comprising a composition containing lutein and zeaxanthin fatty acid esters wherein the composition contains by weight 90–95% of trans-lutein esters, 0–5% of cis-lutein esters and 3.5 to 6% of zeaxanthin esters.

2. The novel xanthophyll ester concentrate as claimed in claim 1, wherein the ratio of trans-lutein:cis-lutein esters in the concentrate ranges at least from 18:1 to 475:1, and including a xanthophyll ester content ranges from 60–80% by weight.

3. The novel xanthophyll ester concentrate as claimed in claim 2, wherein the xanthophyll ester content is 70% by weight.

4. The novel xanthophyll ester concentrate as claimed in claim 1, wherein the concentrate is free from cis-lutein esters and a content of xanthophyll ester ranges from 60–80% by weight.

5. The novel xanthophyll ester concentrate as claimed in claim 4, wherein the xanthophyll ester content is 70% by weight.

6. The novel xanthophyll ester concentrate as claimed in claim 1, wherein the xanthophyll ester concentrate is a lutein enriched composition in a form selected from the group of beadlets, capsules, pellets, ointments, soft gelatin capsules tablets, chewable tablets, or lotions/liquid preparations.

7. A process for the preparation of a xanthophyll ester concentrate as defined in claim 1 comprising:
   (a) admixing an extract or oleoresin containing xanthophyll esters containing lutein and zeaxanthin fatty acid esters with an aliphatic ketonic solvent selected from the group of 2-propanone, 2-butanone, 2-pentanone, or mixtures thereof at a temperature in the range of 10° C. to 30° C. and agitating by stirring to selectively solubilize the nonxanthophyll ester impurities and the cis-lutein esters and lipids present therein while simultaneously enriching the trans-lutein esters content in the resulting mixture;
   (b) filtering the resulting mixture to obtain the trans-lutein enriched xanthophyll ester concentrate in a solid form;
   (c) drying the concentrate under a vacuum at room temperature; and
   (d) preserving the concentrate at a temperature below 20° C. in an inert atmosphere and in airtight opaque containers to prevent degradation of the concentrate.

8. The process as claimed in claim 7, wherein the extract is originated from an xanthophyll ester source that is a marigold flower extract.

9. The process as claimed in claim 7, wherein a temperature employed for admixing the extract with a ketonic solvent is in the range of 15° C. to 30° C.

10. The process as claimed in claim 7, wherein the admixing and agitation in step a) is effected for a period ranging from 2 to 15 hours.

11. The process as claimed in claim 10, wherein the admixing and agitation in step a) is effected for a period of around 10 hours.

12. The process as claimed in claim 7, wherein the temperature employed for drying under a vacuum is in the range of 25° C. to 30° C.

13. The process as claimed in claim 7, wherein the weight to volume ratio of the oleoresin containing xanthophyll esters to the aliphatic ketonic solvent used is a ratio in the range of 1:3 to 1:15.

14. The process as claimed in claims 7, wherein the resulting trans-lutein enriched xanthophyll esters concentrate is made in a form selected from the group of beadlets, capsules, pellets, ointments, soft gelatin capsules, tablets, chewable tablets, or lotions/liquid preparations.

* * * * *